United States Patent
Shchepinov et al.

(10) Patent No.: US 6,455,071 B1
(45) Date of Patent: Sep. 24, 2002

(54) BRANCHED DENDRIMERIC STRUCTURES

(75) Inventors: Mikhail Sergeevich Shchepinov; Edwin Mellor Southern, both of Oxford (GB)

(73) Assignee: Isis Innovation, Ltd. (GB)

( * ) Notice: Subject to any disclaimer, the term of this patent is extended or adjusted under 35 U.S.C. 154(b) by 0 days.

(21) Appl. No.: 09/486,453

(22) PCT Filed: Aug. 27, 1998

(86) PCT No.: PCT/GB98/02578

§ 371 (c)(1),
(2), (4) Date: Feb. 25, 2000

(87) PCT Pub. No.: WO99/10362

PCT Pub. Date: Mar. 4, 1999

(30) Foreign Application Priority Data

Aug. 27, 1997 (GB) ............................................. 9718129

(51) Int. Cl.$^7$ ................................................. A61K 9/14
(52) U.S. Cl. ................... 424/486; 525/420; 435/320.1; 435/455; 514/2; 514/44
(58) Field of Search ................ 424/450, 486, 424/93.2; 525/420; 435/320.1, 455, 6, 325; 514/2, 44

(56) References Cited

FOREIGN PATENT DOCUMENTS

| WO | 9413325 | 6/1994 |
|---|---|---|
| WO | 9619240 | 6/1996 |

OTHER PUBLICATIONS

Roy, R. (1996) "Glycodendrimers: a new class of biopolymers" *Polymer News* 21:226–232.

Shchepinov, M.S. et al. (1997) "Oligonucleotide dendrimers: synthesis and use as polylabelled DNA probes" *Nucleic Acids Res.* 25(22):4447–4454.

Hudson, R.H.E. et al. (1993) "Nucleic acid dendrimers: novel biopolymer structures" *J. Am. Chem. Soc.* 115:2119–2124.

Zeng, F. et al. (1997) "Dendrimers in supramolecular chemistry" *Chem. Rev.* 97(5):1681–1712.

Majoral, J.P. et al. (1996) "Arbres moléculaires (dendrimères) phosphorés: une future forêt d'applications" *Actual. Chim.* 4:13–18.

Majoral, J.P. et al. (1996) "Phosphorus–containing molecular trees (dendrimers): A future forest of applications" *Actual. Chim.* 4:13–18.

Hudson, R.H.E. et al. (1993) "Nucleic acid dendrimers: novel biopolymer structures" *J. Am. Chem. Soc.* 115:2119–2124.

Anderson, Human gene therapy, Nature vol. 392, Apr. 1998, pp. 25–30.*

Verma et al., Gene therapy–promises, problems and prospects, Nature vol. 389, Sep. 1997, pp. 239–242.*

* cited by examiner

*Primary Examiner*—Dave T. Nguyen
(74) *Attorney, Agent, or Firm*—Saliwanchik, Lloyd & Saliwanchik (57) ABSTRACT

The present invention provides new reagents and methods which allow the assembly of large, branched structures from simple but versatile building blocks. The invention discloses dendrimers obtainable by the reaction of a core molecule having at least two reactive groups sequentially with doubling, trebling or more, branching synthons and optionally also with nonbranching synthons, to provide a multimeric structure having branched units and optionally also non-branched units, and a plurality of blocked or unblocked functional groups at the outer ends of the structure.

2 Claims, 7 Drawing Sheets

Alternative Tag System

BRANCHED DENDRIMERIC STRUCTURES

FIELD OF THE INVENTION

This invention relates to the production of branched dendrimeric structures using phosphoramidite chemistry, and to the uses of the dendrimers.

BACKGROUND OF THE INVENTION

Since their first synthesis, dendrimers have attracted considerable attention as a new branch of polymer science. Two basic strategies for the synthesis of these structures have been proposed: divergent, with the structure grown up from the centre to the periphery; and convergent, growth of the molecule from the periphery to the centre.

One of the most important parameters governing a dendrimeric structure and its generation, is the number of branches generated at each step; this defines the number of repetitive steps necessary to build up the desired molecule and the density of the groups at the periphery. The main properties of the dendrimeric molecule are determined by the functional end groups of moieties on its outer shell. Many applications proposed for dendrimers exploit the high density and the large number of these groups.

For example, dendrimers with a positively charged outer surface interact strongly with nucleic acid, a property which has been used recently for the transport of nucleic acids through the membranes of living cells; see Boussif et al, Proc. Natl. Acad. Sci., USA, (1995):92:7297–7301.

Branched (dendrimeric) oligonucleotides can be used to amplify radioactive or fluorescent signals in hybridisation tests. Such amplification may be particularly important in in situ hybridisation and in the emerging techniques which exploit oligonucleotide arrays, where the signal is limited by the surface density of the oligonucleotides or the target molecule.

Phosphitamide reagents have been described which double the amount of reactive 5'-hydroxyl groups after each condensation step, thus giving $2^n$ reactive OH groups after n condensations, and they have been used in combination with biotin, fluorescein, pyrene and other phosphitamide synthons for multiple 5'-labelling of oligonucleotides. However, all these compounds have a particular disadvantage in that they result in highly dense structure which results in a high concentration of reporter groups, leading to self-quenching of fluorescence.

SUMMARY OF THE INVENTION

The present invention provides new reagents and methods which allow the assembly of large, branched structures from simple but versatile building blocks. The invention discloses dendrimers obtainable by the reaction of a core molecule having at least two reactive groups sequentially with doubling, trebling or more, branching synthons and optionally also with non-branching synthons, to provide a multimeric structure having branched units and optionally also non-branched units, and a plurality of blocked or unblocked functional groups at the outer ends of the structure.

In particular, the present invention discloses a dendrimer, wherein the core molecule and/or the synthons have the formula wherein $F^1(P^1)$ is an optionally-protected functional group; the n $F^2(P^2)$ groups are the same or different optionally-protected functional groups reactive with a functional group $F^1$; $L^1$ and $L^2$ are the same or different linkers; J is a junction group; and n is 1 (a non-branching synthon), 2 (a doubling, branching synthon), 3 (a trebling, branching synthon) or more.

DESCRIPTION OF THE INVENTION

The present invention provides synthons which can be used to synthesise a wide range of dendritic assemblies with defined structure, chemistry and physical properties. Divergent synthesis (see Ref. 1) will usually be conducted sequentially, building up as many branches as are desired, to give a structure in which any one limb is of the type: Core-(((Branch-Joint)$_n$)$_m$-Terminus)$_1$. A distinguishing feature of a dendritic structure formed from these synthons is that it has several termini and only one path can be traced through its branches from one terminus to another, or from the core group to a terminus.

A feature of the core molecule is that it should have at least two sites from which chemical growth can be initiated and preferably a site of attachment to a solid support through a spacer molecule. The attachment site may be cleavable to allow the assembly to be removed from the support when synthesis is complete, or it may be used as an anchor to tether the assembly to the support. The core should be chemically inert to the synthetic procedures used during synthesis of the assembly, and to the conditions it will meet during the application. The reagent used to form this first generation of the dendrimer will be a branching (type II) synthon.

A feature of a branching synthon (type II) is that it should have at least three coupling sites, which will be joined at the junction group (J) which may be a multivalent atom such as carbon, silicon, phosphorus or nitrogen, or a ring such as a six-membered aromatic ring.

The linkers, the groups between the junctions and the functional groups, are an important feature of the building blocks. Properties of linkers may include but are not confined to: length; flexibility; solvation properties; degree of branching; chemical functionality; chirality. The linkers that may be used include, but are not limited to, polymeric chains of aliphatic, aromatic and alkoxy residues.

Figure 3:
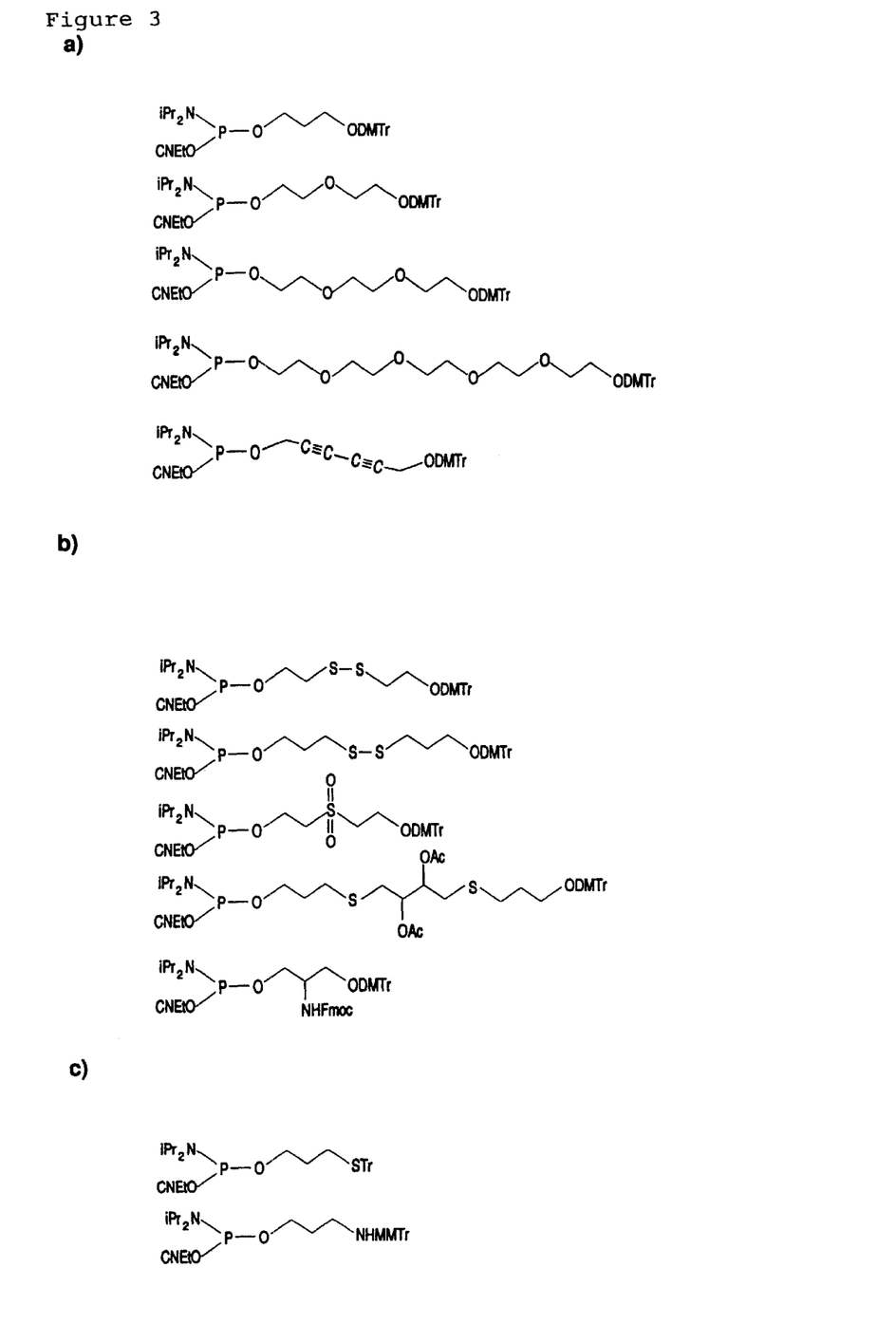
FIG. 3 illustrates examples of different linkers (a and b) and examples of synthons with different reporter groups.

The branches of the building blocks determine the main structural features of the assembly. They may be made by stepwise coupling of a non-branching (type I) synthon to give greater choice of length and composition. In certain applications a functional group may be included within the linker to give it desirable chemical or physical properties. For example, including a sulphydryl group would enable the linkers to be crosslinked by oxidation after synthesis to stiffen and strengthen the assembly; hydrogen donors or acceptors or changed groups may also be included to modify the structure (FIG. 3).

The functional groups, $F^1$ and $F^2$, determine the main chemical properties of the synthons; they will be chosen according to the structural requirements of the dendrimer. Groups may be included which are activated for chemical coupling, for example: hydroxyl; amino; sulphydryl; phosphate; phosphitamide; etc; or derivatives thereof. For example, $F^1$ may include a phosphorous atom in the P=S form and other in the P=O form, or vice versa, whereby the balance of the two forms, and thus the purity of the product, can be checked.

During synthesis of the assembly, groups $F^2$ at the ends of the building blocks act as the coupling site for the addition of a further building block, or the addition of terminal groups.

The protecting groups prevent reaction of functional groups, $F^2$, during coupling. The wide choice of available protecting groups provides a great deal of versatility; in particular, it is possible to remove protecting groups selectively, leaving other groups in place. Thus, during stepwise synthesis, it is possible to elongate from selected sites, individually or multiply, in sequence; or to elongate one site leaving others to be treated at a later stage. The manipulation of protecting groups is an important, through optional, component of the methods of the present invention.

Protecting groups and the methods of removal may include but are not confined to groups which can be removed by: acid; base; fluoride ions; hydrazine; light; and by hydrogenation. See also Reference 3.

The ends of the branches of the final dendrimer are determined by the synthon used in the last step, which may be of type I or type II. The functions on the ends of these synthons will form the outermost layer of the dendrimer, determining its chemical and physical properties. They may include but are not confined to: charged; hydrophilic; hydrophobic; hydrogen-donor or acceptor; metal-coordinating; reducing; and oxidising groups.

The branches of the dendrimer need not be all of the same length, e.g. following non-reaction at least one branch. This may produce a dendrimer with a surface that is convex or concave.

A solid support may be used during synthesis, to simplify separation of the product from reagents. When an array of components is to be synthesised on a planar surface, these may be means to segregate the surface into defined areas to which the chemical reactions can be directed. Combinatorial synthesis may be carried out on a particulate solid support using split synthesis strategies; see Ref. 4. The support is divided into separate reaction compartments for the addition of different reagents at each stage in the synthesis and then combined and mixed before being split for the next round of coupling. In this way, each molecule on any particle goes through the same set of procedures, but each particle may go through a different set of procedures.

It is important that the reactive groups on the solid support are able to support the synthesis of the desired assembly and above to take part in any interaction necessary for applications. Steric crowding will make synthesis or interactions ineffective if the groups are either too close together or too close to the surface. Thus, the solid support may be derivatised with a spacer molecule for each synthesised assembly.

The support materials that may be used include but are not confined to: glass e.g. controlled-pore glass; plastics etc. Spacers that may be used include but are not confined to polymeric chains of: aliphatic, aromatic, alkoxy residues.

The protecting groups ($P^1$ and $P^2$) may be selected from a diverse range of known protecting groups. For example, the groups may be a dimethoxytrityl group, a fluorenylmethoxy carbonyl group or a levulinyl group.

Rational Approaches to Molecular Design

The chemical approach embodied in the present invention simplifies the synthesis of molecular assemblies and the fabrication of devices with defined chemical and physical properties.

There are two stages to the rational design of a chemical entity with desired properties: it is conceived as a model which is built from components with known properties; it is then synthesised in the laboratory, normally using a wide range of procedures if the structure is complex. The two processes may be interactive: as the project proceeds, there are cycles of modelling and synthesis until a compound with the desired properties is created and the process for its manufacture has been optimised.

The advantages of the present approach are: it simplifies the modelling process, as the properties of the building blocks—bond lengths, angles and stiffness, hydrophobicity and other affinities —will be well characterised; it simplifies synthesis, as the chemical steps are relatively few; it opens the way to novel structures possible only by this approach.

The approach focuses on the key components of the structure, i.e. core, linkers and surface groups. The surface groups will often be functional groups that must have a well-defined spatial relationship, as for example, the active site of an enzyme. They will define the surface properties of the final assembly. The core and the linkers are important mainly in so far as they affect the properties of the surface and influence the assembly process. The design of the core and the linkers determines the shape of the surface and number, the position and disposition of the key functional groups. They are important determinants of the architecture and properties of the assembly.

For example, if the assembly is to be spherical, the core will be chosen to allow symmetrical growth from the centre and linkers will be used which have the same molecular volume at each position in the growing molecule.

Figure 5:
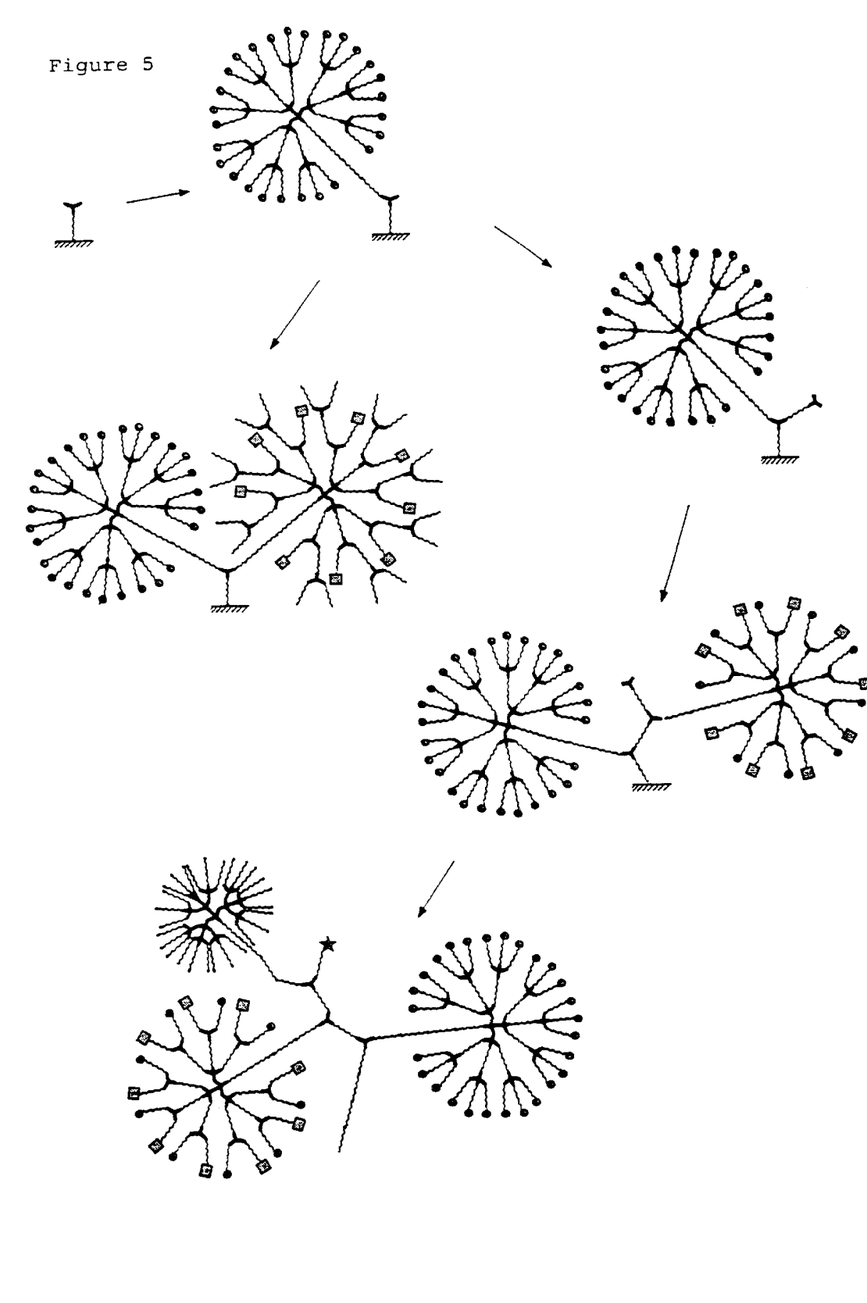
FIG. 5 illustrates the synthesis of conjugated dendrimers.
Figure 6:
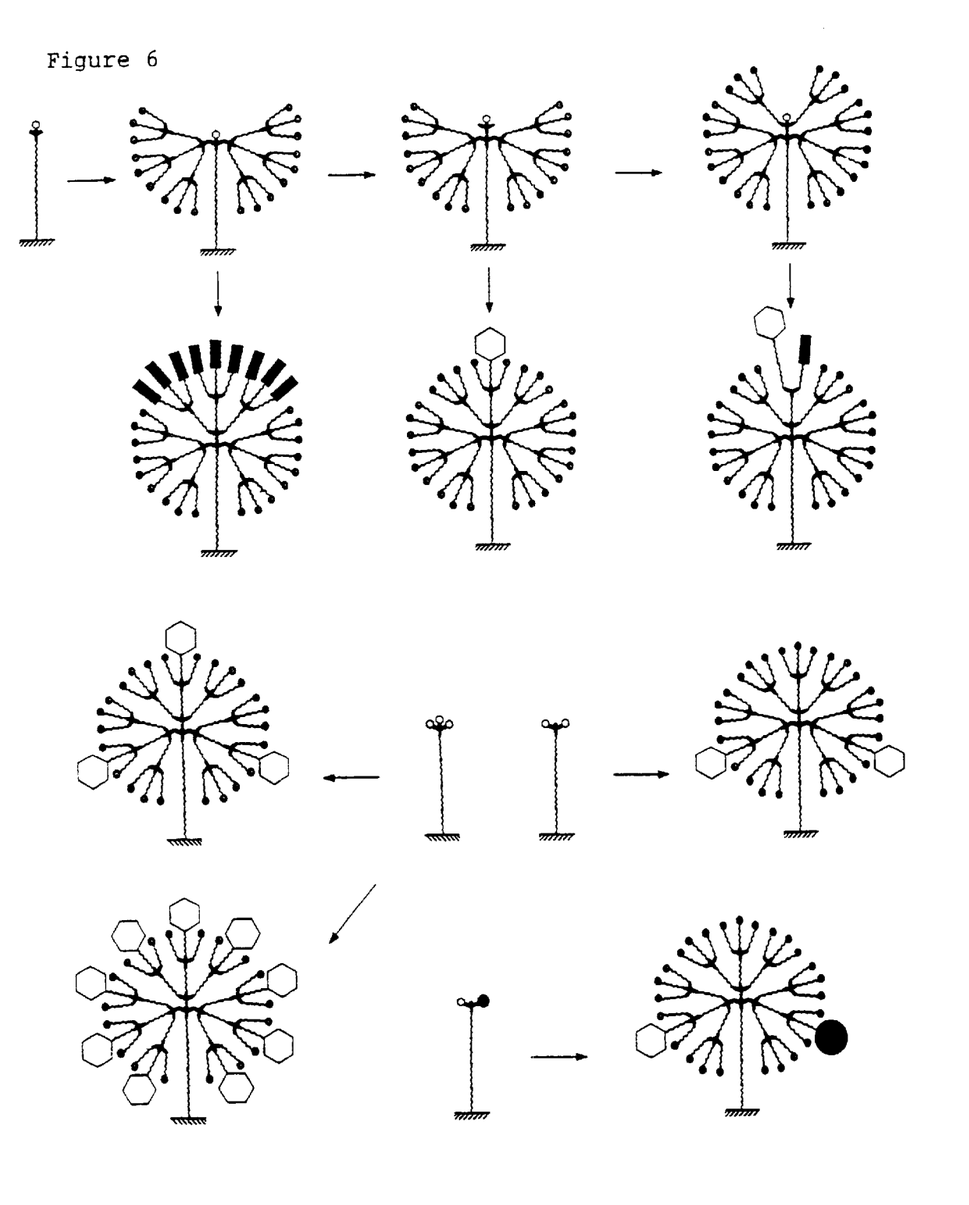
FIG. 6 illustrates oligofunctionalised dendrimers.

There are many ways in which the functional groups can be arranged on the surface. It may be desirable to have one side of the sphere coated with one group, and the other side with another. This is readily achieved using the process illustrated in FIGS. 5 and 6. Alternatively, it may be desirable to have both of two functional groups uniformly disposed over the whole of the surface. FIG. 5 makes clear how this can be achieved using a doubler with different two protecting groups. A single unit of the two functional groups can be placed in any geometrical relationship by choosing the appropriate synthetic path as illustrated in FIG. 6. In general, this can be extended to m different functionalities. In a simple embodiment of the invention, the outermost units are each derived from branching synthons with 2 or 3 or more different functional groups or protecting groups, thereby allowing coupling of 2, 3 or more moieties. If desired, such moieties can themselves be branching units with different groups, thereby increasing the available variety of functionalities which can be displayed on the surface.

Alternatively, it may be desirable to introduce a pocket into the structure. This is readily achieved by extending most of the branches, leaving one or more branches unextended, as illustrated in FIG. 6, or by using cleavable linkers in the branches.

Figure 4:
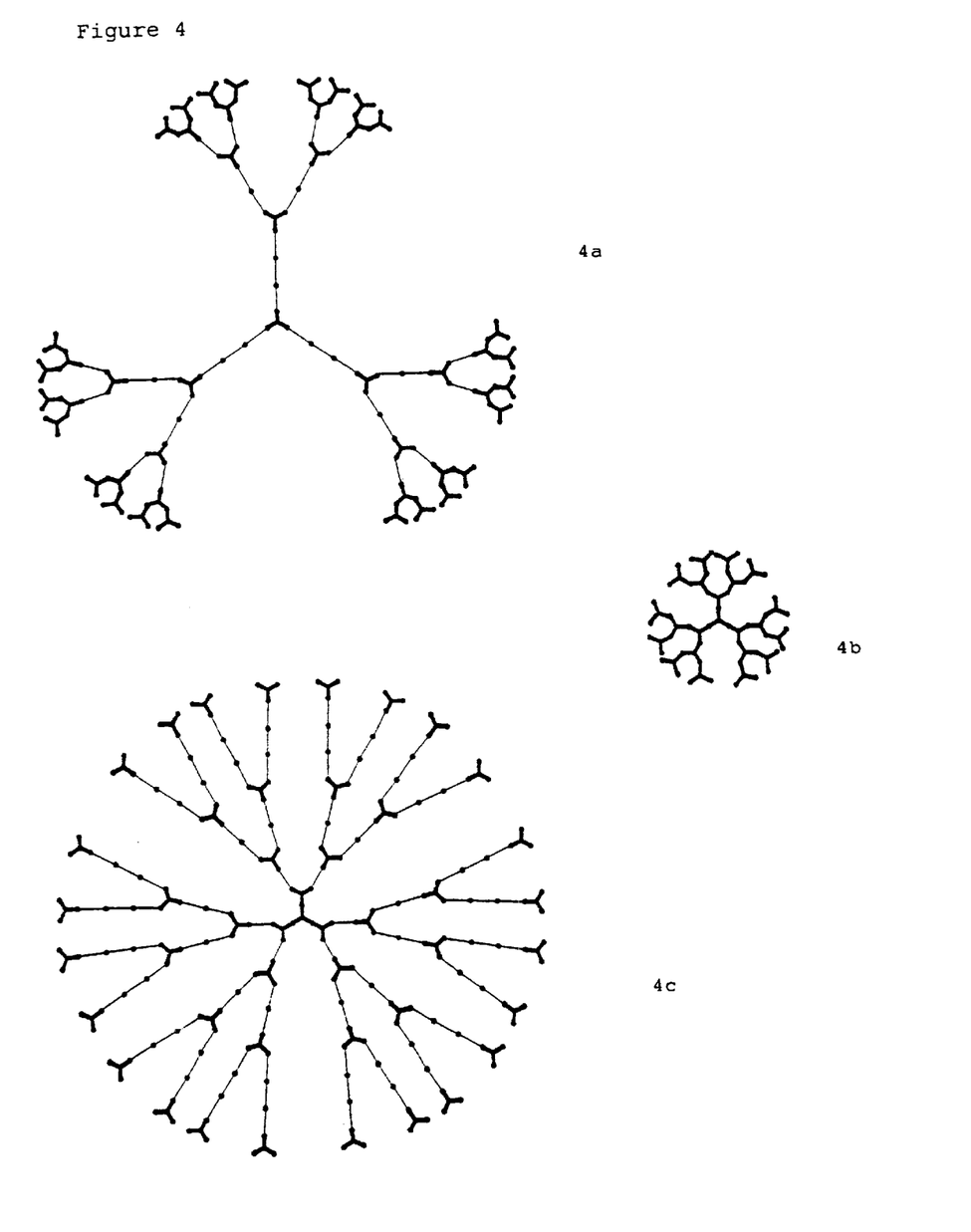
FIG. 4 illustrates different dendrimer structures.

Clearly, at any stage, the bulk properties and the shape of the assembly can be modified by varying the nature of the linker; see e.g. FIG. 4.

Combinatorial Approaches to Molecular Design

Figure 7:
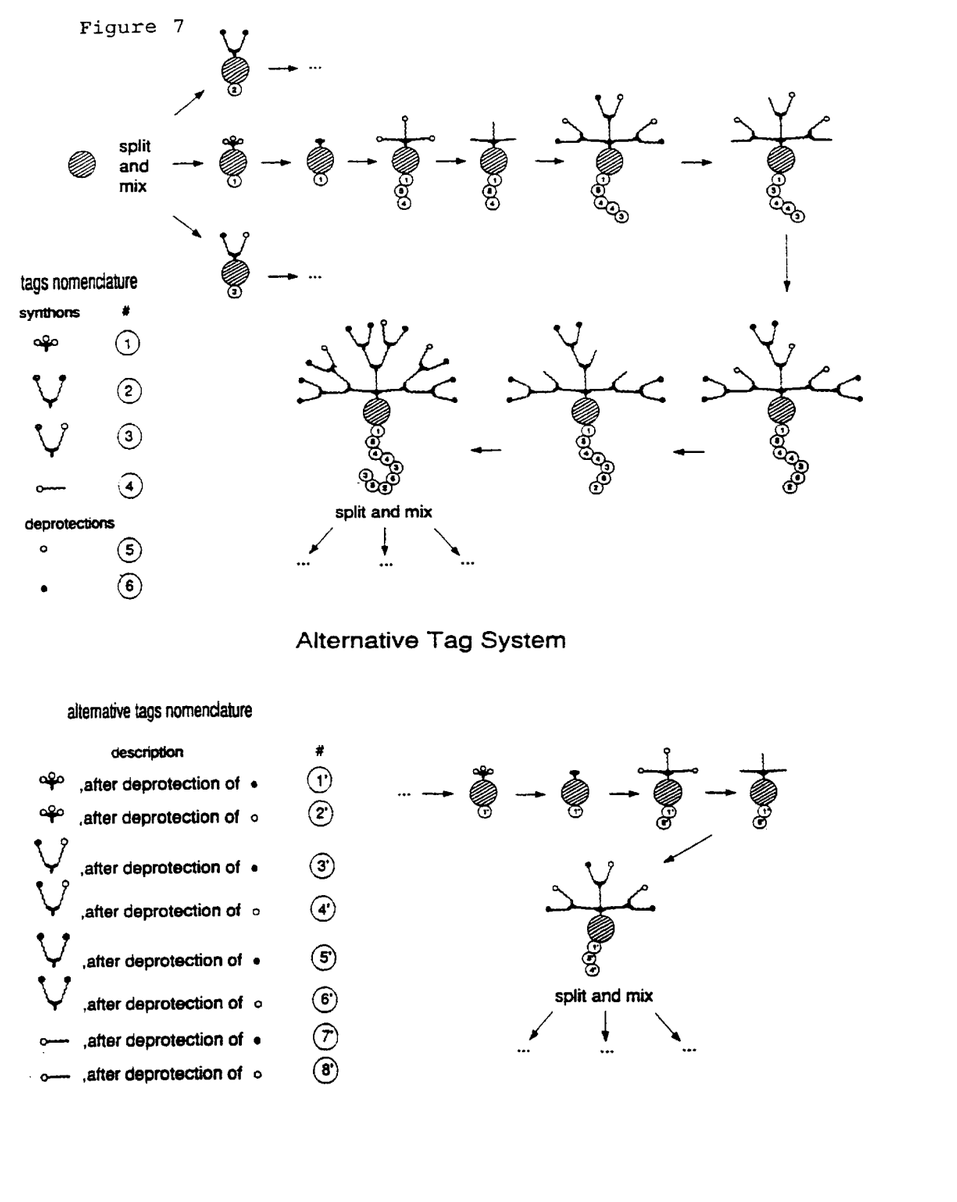
FIG. 7 illustrates a combinatorial approach to the synthesis of dendrimers.

An alternative to the rational approach to molecular design exploits the coupled processes of combinatorial synthesis and selection of compounds with the desired properties. Large numbers of compounds are produced either as mixtures, or as arrays in which the different compounds are synthesised in parallel in defined areas on the surface of a solid support. Typically, useful members are identified by some empirical test: for example, by applying a ligand to the set to find or select those members which bind most strongly. The compounds may be identified by analysing them directly: in the case of arrays, the compounds will be identified from their positions on the surface. The products of split and mix strategy (see Ref. 4) may be identified from "tags", synthesised in parallel with the functional compound: for example, each step in the synthesis of the functional compound is tracked by the addition of a specific tag to the particle which carries the compound e.g. as shown in FIG. 7. The tags are chosen to be easily identifiable. For example, oligonucleotide tags, which can be amplified by PCR, and read by conventional sequence analysis, have been suggested for use with peptide libraries. Tags may also be read by mass; see Ref. 5. Libraries produced by conventional coupling chemistries generate linear molecules—most commonly peptides. Powerful though it is, the combinatorial approach has limitations when applied to complex linear molecules such as polypeptides.

To make a chain of 100 amino acids by linear synthesis requires 100 coupling steps, producing a backbone of 400 atoms. By contrast, using a trebler as defined herein, a globular molecule of 160 linked atoms is produced after only three couplings and 800 atoms after four couplings. The reagents which are the subject of this invention are well adapted to create different structures, particularly molecules with a different disposition of groups at their surfaces, by combinatorial chemistry.

Many therapeutic agents and most molecular targets for therapeutic intervention are macromolecules. For example, many conventional drugs target large proteins such as cell surface receptors: the new therapies based on antisense technologies target nucleic acids. Many of these targets have more than one potential binding site. It has been shown that mRNAs have multiple binding sites for antisense oligonucleotides; see Ref. 6. Reagents targeting the different sites act more effectively when bound together than when they are added as separate molecules. Further, binding strength is enhanced if they are spaced by a linker of optimum length; presumably adapted to the geometry of the multiple binding sites. Clearly, the branched molecules which are the subject of the present invention offer novel ways of presenting multiple ligands with different geometries. Moreover, the reagents and methods offered by the invention allow combinatorial synthesis which can be adapted to the fabrication of arrays of reagents on a solid support, each member of which presents the multiple ligands at a unique address on the surface. Protocols for the fabrication of such arrays described in the scientific literature (see Ref. 7) are readily adapted to the use of branching synthons.

Applications

Molecular Adaptors

In microfabrication, assembly is made difficult by the small size of the components. This problem can be solved if the parts can be made to self-assemble spontaneously. This can be achieved by providing the components to be assembled with "complementary surfaces": e.g. two surfaces which are hydrophobic will stick to each other in a medium which is hydrophilic and vice versa.

A more complex set of surfaces may be achieved by derivatising them with oligonucleotides of defined sequence. The rules of Watson-Crick base-pairing allow for the definition of an almost unlimited number of complementary surfaces. An extension of this example allows for the segregation of a planar surface into many zones, each with its own "adhesive address", using well established ways for creating arrays of oligonucleotides on a surface. In this way, components carrying oligonucleotides of different sequence can be directed to specific locations on the surface. Examples of oligonucleotide dendrimers are contained in Shchepinov et al, Nucleic Acids Research, 1997; 27(22) :4447–4454.

Surfaces with Defined Physical and Chemical Properties

The properties of a surface, its wettability, frictional properties, adhesiveness etc.—depend on its chemical composition. The present invention offers a simple way of defining the chemical composition to fine limits within a wide range. For example, the hydrophobicity of a surface could be fine-tuned by coupling functional groups with different properties in different proportions. The difference between a surface created in this way and one created by mixing components with different properties is that the surface would be uniform at the molecular level, rather than a statistical representation of a mixture. This difference becomes increasingly important as the dimensions of devices approach the molecular scale, where the composition of a small area of a statistical mixture may diverge substantially from the average.

Molecules suitable for creating surfaces with defined properties are exemplified below. As in the previous example, zones with different affinities could be created by using different compositions of functional groups.

Molecules with Mixed Reporters

Fluorescence is becoming the method of choice for tagging ligands used in biochemical and other analyses; see Ref. 8. One of its advantages is the possibility of using tags with different absorption and/or emission spectra to distinguish different ligands. The range of fluorescence wavelengths may be greatly extended if different fluorescent moieties in different proportions were attached to the same ligand (FIGS. 5 and 6).

Other fluorescence detection systems exploit the process of energy transfer: in this system, one moiety is excited by the incident beam and then transfers its energy to the other from which it is emitted as light. The distance and orientation of the energy donor and acceptor are critical to efficient energy transfer. These systems will be easy to design and manufacture using the reagents described. A further advantage is that it is possible to increase the sensitivity by incorporating multiple fluorophores on the same molecule.

Molecular Mimetics

Synthesising complex compounds, such as those used as drugs, or compounds which mimic the properties of naturally occurring compounds, is a major activity of the pharmaceuticals industry. Such syntheses can be difficult, and for some substances, such as proteins, may be impossible. The reason for this is that the protein is a linear copolymer of a number of different units. The activities or binding properties of most proteins are determined by relatively few residues but it is important for function that these crucial residues are placed correctly in the structure, and that the structure can adopt particular configurations in response to interactions with other molecules. Proteins are made almost wholly of amino acids, not because amino acids have particularly favourable properties, but because evolution has provided a way of making a wide range of complex molecules from these relatively few building blocks. The linear primary structure is imposed by the constraints of the biosynthetic pathway which links the genetic code in the DNA to the amino acid sequence in the DNA. The chemist is not so constrained and can think of structural solutions, and synthetic pathways which involve non-linear codes. That other molecular types can do the same job as amino acids is illustrated by the ribozymes, which are catalytic RNAs, and by synthetic compounds which mimic the activation complexes of a number of enzymes.

Most of the amino acid residues in an enzyme provide the architecture and flexibility needed to form the critical amino acids of the active site into the correct configurations adopted in the different stages of the interaction with substrate, intermediate and product. One objective of the present invention is to provide simpler means to synthesise the scaffold. To give some idea of the potentially greater simplicity of branched versus linear synthesis, consider an assembly of 100 units—the approximate size of a small globular protein. Linear synthesis requires 99 coupling steps. Branched synthesis using a doubler requires six coupling steps to achieve a molecule of the same size.

Controlled Drug Release

There are major benefits to introducing drugs in a way which releases them slowly to the site of action, rather than in a single concentrated burst. Dendrimers comprising multiple drug units attached to a core through arms which are digested by intracellar enzymes at different rates offer a new way to achieve staged release.

Varying Numbers of End-groups and of Linkers

To give an idea of the variety of structures that can be created using branching synthesis, we calculate here the number of different structures that can be generated using branching synthons with just two or three different protecting groups and/or linker arms.

The simplest case is of units which double the number of branches at each step. In this case, there may be two different protecting groups on the ends of the two branches, which are differentially removed at each split of the split/mix scheme; or the arms of the branches may be different (e.g. different length). Designating the different branches a, b, the numbers of variants are:

First generation: aa, ab, bb

Second generation: aa.aa, aa.ab, aa.bb, ab.bb, bb.bb, ab.ab (Note that aa.bb=bb.aa≠ab.ab as the spacings of the groups and/or the linkages will be different at the surface.)

The numbers of variants are 3, 6, 21, 231, 26796, $3.59e^8$ and $6.44e^{16}$ in the first to the seventh generations. In general, $V_{n+1}$, the number of variants after n+1 generations, is $\frac{1}{2}V_n(V_n+1)^2$.

For a trebler with three variant end-groups or linkers, the growth of possible variant surfaces is much faster, related to the cube of the preceding generation. First generation: aaa, aab, aac, abb, abc, acc, bbb, bbc, bcc, ccc. In general, $V_{n+1}$, the number of variants after n +1 generations, is $\frac{1}{6}V_n(V_n+1)(V_n+2)$. There are 220 variants in the second generation, around two million in the third and $10^{18}$ in the fourth generation.

| | Total number of ends and variants | | | |
|---|---|---|---|---|
| | | | Trebling | |
| Doubling Generation | No. of ends | No. of variants | No. of ends | No. of variants |
| 1 | 2 | 3 | 3 | 10 |
| 2 | 4 | 6 | 9 | 220 |
| 3 | 8 | 21 | 27 | 1.8e6 |
| 4 | 16 | 231 | 81 | 9.7e17 |
| 5 | 32 | 2.7e4 | 243 | |
| 6 | 64 | 3.6e8 | 729 | |
| 7 | 128 | 6.4e16 | 2187 | |

The protocol needed to generate these large numbers of variants is a simple split/mix scheme. For the doubler: three lots of solid support are derivatised with each of the three monomers, aa, ab and bb. These are mixed, divided in three and the three monomers coupled to each of the three lots. And so on. Similarly with the trebler, but in this case there are ten lots and ten couplings at each step.

Much greater structural variation in the dendrimer comes from combining linker with coupling or protective group variation. For example, for doublers with two linkers the two coupling/protective groups there are ten different monomers: a1a1, a1a2, a1b1, a1b2, a2a2, a2b1, a2b2, b1b1, b1b2, b2b2. The second generation would comprise 55 types.

The product of the split/mix schedule is a mixture of dendrimers with a range of shapes and/or surfaces differently populated with chemical moieties. Such mixtures may then be functionalised with a range of different groups to give different "families" of dendrimers. For example, in the case of surfaces differentially populated with two protecting groups, a and b, the mixture could have group a removed for coupling with group W in one batch and for coupling with group X in another; protecting group b could be removed before the coupling of groups y and z. This would lead to surfaces derivatised with w+y, w+Z, X+Y and X+Z.

Clearly the growth in numbers of variants with branching monomers is much faster per generation than the corresponding rate for linear monomers. With four monomers, for example nucleotides, the number of possible sequences after six couplings is $4^6$=4096. Fourteen generations are needed to make the number of variants reached by the doubler in six generations.

The invention is now further illustrated by the following Examples, with reference to the accompanying drawings.

EXAMPLES

Tetrafunctional Building Blocks

Figure 1:
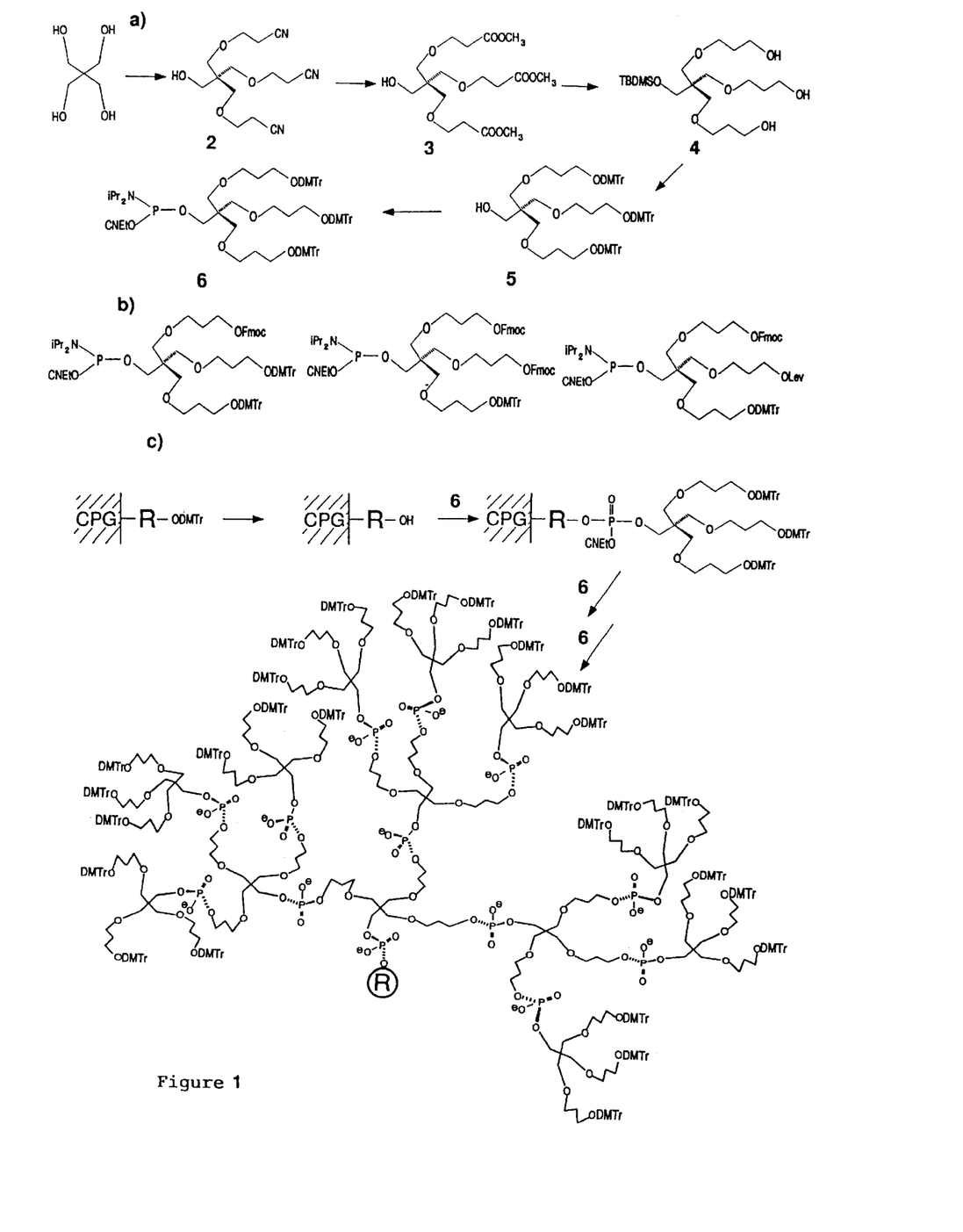
FIG. 1 illustrates the synthesis of different trebling reagents used in the invention and the synthesis of a dendrimer using the trebling reagents.

A series of compounds have been made with four branched chains of different composition, thus giving four coupling sites, functionalised at the ends with different groups, and with different protective groups (FIG. 1a). The compounds and their properties are:

tris-2,2,2-[(cyanoethoxy)methyl]ethanol(2). Acrylonitrile (100 ml, 1.55 mol) was added to a stirred mixture of pentaerythrite (1, 68 g. 0.5 mol) and sodium hydroxide (2.5 g, 0.075 mol) in 75 ml of water at RT. The mixture was then stirred at 50° C. overnight. The solution obtained was neutralized with 5% HCl and washed 3 times with 200 ml of ethyl acetate. The combined organic phase was evaporated in vacuo to give about 120 g of colorless syrup which was purified by flash chromatography (chloroform) to give 94 g (63.7%) of 2 as a colourless syrup. Rf: 0.68 (methanol:methylene chloride, 1:9, detection of TLC in I2 vapour). (For tetrakis-product: Rf=0.9). Calculated for $C_{14}H_{21}N_3O_4$: 295. Mass-spectrum, MALDI-TOF: 296.217 (MI+H$^+$), 318.475 (MI+Na$^+$), 334.474 (MI+K$^+$), IR:2240 cm$^{-1}$ (C≡N). Calculated for the tetrakis-product $C_{17}H_{24}N_4O_4$: 348. Mass-spectrum, MALDI-TOF: 349.452 (MI+H$^+$)

tris-2,2,2-{[(methoxycarbonyl)ethoxy]methyl}ethanol (3). A solution of 2(15 g, 0.05 mol) in HCl-saturated methanol (200 ml) was refluxed for 2.5 h. To this mixture 10 ml of H2O and 5 ml of conc. HCl were added and the mixture was stirred for 15 min. After addition of 400 ml of H2O, the mixture was extracted with ethyl acetate (3×150 ml), combined organic fractions were washed with NaHCO3 sat. (4×200 ml), brine, dried over Na2SO4 and evaporated in vacuo to give 15 g (75%) of 3 as a colourless oil. Rf: 0.62 (methanol:chloroform, 1:30, detection of TLC in I2 vapour). IR: disappearance of the band at 2240 cm$^{-1}$ (C≡N). Calculated for C17H30O10: 394. Mass-spectrum, MALDI-TOF: 394.972 (MI+H$^+$), 416.934 (MI+Na$^+$), 432.892 (MI+K$^+$).

tert-butyldimethylsilyl-[tris-2,2,2-(5-oxy-2-oxa-pentyl) ethanol] (4). To the alcohol 3 (13.5 g, 34 mmol, coevaporated with dry pyridine) in 150 mlof anhydrous pyridine TBDMSCl (6 g, 40 mmol) was added and the mixture was stirred overnight at RT. Mass-spectrum (MALDI-TOF) of the reaction mixture showed complete conversion of initial alcohol into silylated product. Rf: 0.83 in methanol:chloroform, 1:30 and 0.91 in methanol:chloroform, 1:9, detection of TLC in I2 vapour. Calculated for C23 H44O10Si: 509; found: 508.882 (MI), 530.864 (MI+Na$^+$), 546.819 (MI+K$^+$). The reaction mixture was evaporated to dryness, residue dissolved in 200 ml of ethyl acetate, washed with NaHCO3 sat. (4×200 ml), brine, dried over Na2SO4 and evaporated in vacuo to give a silylated triester as a colourless oil (17.3 g, 98%), 17 g (33 mmol) of this triester was dried in vacuo over P2O5, dissolved in 20 ml of anhydrous THF and added during 40 min. to the stirred ice-cold suspension of LiAlH4 in 350 ml of anhydrous THF. The mixture was then stirred for another 45 min on ice bath and 1.5 h at RT. 45 ml of 15% solution of NaOH in water was added during 20 min. The residue was decanted and washed with THF (3×30 ml). Combined THF fractions were diluted with water (150 ml) and carefully neutralized with diluted HCl. The mixture was evaporated and purified by flash chromatography (methanol:chloroform, 1:30 to 1:6) to give 9.5 g (67%) of colorless oil. Rf: 0.49 (methanol:chloroform, 1:9, detection of TLC in I2 vapour). Calculated for C20H44O7Si: 425. Mass-spectrum. MALDI-TOF: 426.005 (MI+H$^+$), 448.131 (MI+Na$^+$).

tert-butyldimethylsilyl-{tris-2,2,2-[3-(4,4'-Dimethoxytrityloxy)propyloxymethyl]ethanol} Triol 4 (2 g, 4.7 mmol) was dried by coevaporation with anhydrous pyridine and dissolved in 60 ml of it. DMTrCl (6 g, 17.75 mmol) was added under stirred for 2 h, after which time 750 mg of DMTrCl, catalytic amount of DMAP and 1 ml of EDIP were added to this stirred mixture. In 5 h, 1 ml of water was added to the reaction mixture, it was stirred for another 10 min. and evaporated to an oil, dissolved in 200 ml of ethylacetate, washed with NaHCO3 sat. (4×200 ml), brine, dried over Na2SO4 and evaporated in vacuo. The resulting oil was purified by flash chromatography (hexane:dichloromethane, 1:3 to dichloromethane) to give 3.5 g (58%) of white solid. Rf: 0.75 (chloroform with traces of Et3N), 0.86 (hexane:ethylacetate, 3:1, traces of Et3N). Calculated for C83H98O13Si: 1331,6. Mass-spectrum, MALDI-TOF: 1355.62 (MI+Na$^{+)}$ $^1$H-NMR (CDCl3, δ, md): 7.5–6.7 (m, 39 H, arom.), 3.73 (s, 18 H, OCH3), 3.39 (t, 6 H, DMTrOCH2), 3.23 (s, 6 H, (OCH2)3C), 3.08 (t, 6 H, CH2O), 1.79 (quin., 6 H, CH2CH2CH2), 1.58 (s, 2 H, CH2OTBDMS), 0.88 (s,9 H, tBu), 0.05 (s, 6 H, CH3).

tris-2,2,2-[3-(4,4'-Dimethoxytrityloxy)propyloxymethyl] ethanol (5). Silylated compound (2.25 g, 1.7 mmol) was dissolved in 40 ml of standard 1.0 M TBAF solution in THF and stirred for 6 h. Ethylacetate (150 ml) was added and the mixture was washed with NaHCO3sat. (4×200 ml), brine, dried over Na2SO4, evaporated and the resulting oil was purified by flash chromatography (hexane:ethylacetate, 3:1 to 1:1, traces of Et3N) to give 1.8 g (88%) of white solid. Rf: 0.4 (hexane:ethylacetate, 3:1, traces of Et3N). Calculated for C77H84O13: 1216.5. Mass-spectrum, MALDI-TOF: 1241.64 (MI+Na+). $^1$H-NMR (CDCl3, $\delta$, md): 7.5–6.75 (m, 39 H, arom.), 3.77 (s, 18 H, OCH3), 3.45 (t, 6 H, DMTrOCH2), 3.3 (s, 6 H, (OCH2)3C), 3.1 (t, H, CH2O), 2.78 (br. s., 1 H, OH), 1.8 (quin., 6 H, CH2CH2CH2), 1.65 (br. s, 2 H, CH2OH).

tris-2,2,2-[3-(4,4'-Dimethoxytrityloxy)propyloxymethyl] ethyl-N,N-diisopropylaminocyan ethoxyphosphoramidite (6). The alcohol 5 was phosphitylated using chloro [diisopropylamino]-β-cyanoethoxyphosphine as previously described elsewere and purified by flash chromatography (hexane:ethylacetate, 4:1, traces of Et3N) to give the title compound in 75% yield. Rf: 0.55 (hexane:ethylacetate, 3:1, traces of Et3N). Calculated for C86H101N2O14P:1414.9. Mass-spectrum, MALDI-TOF: 1413.22 (MI-H+). $^{31}$P-NMR (CH3CN:CD3CN, 1:1, int. standard: 80% H3PO4, $\delta$, m.d.) :151.312.

Trifunctional Building Blocks

Figure 2:
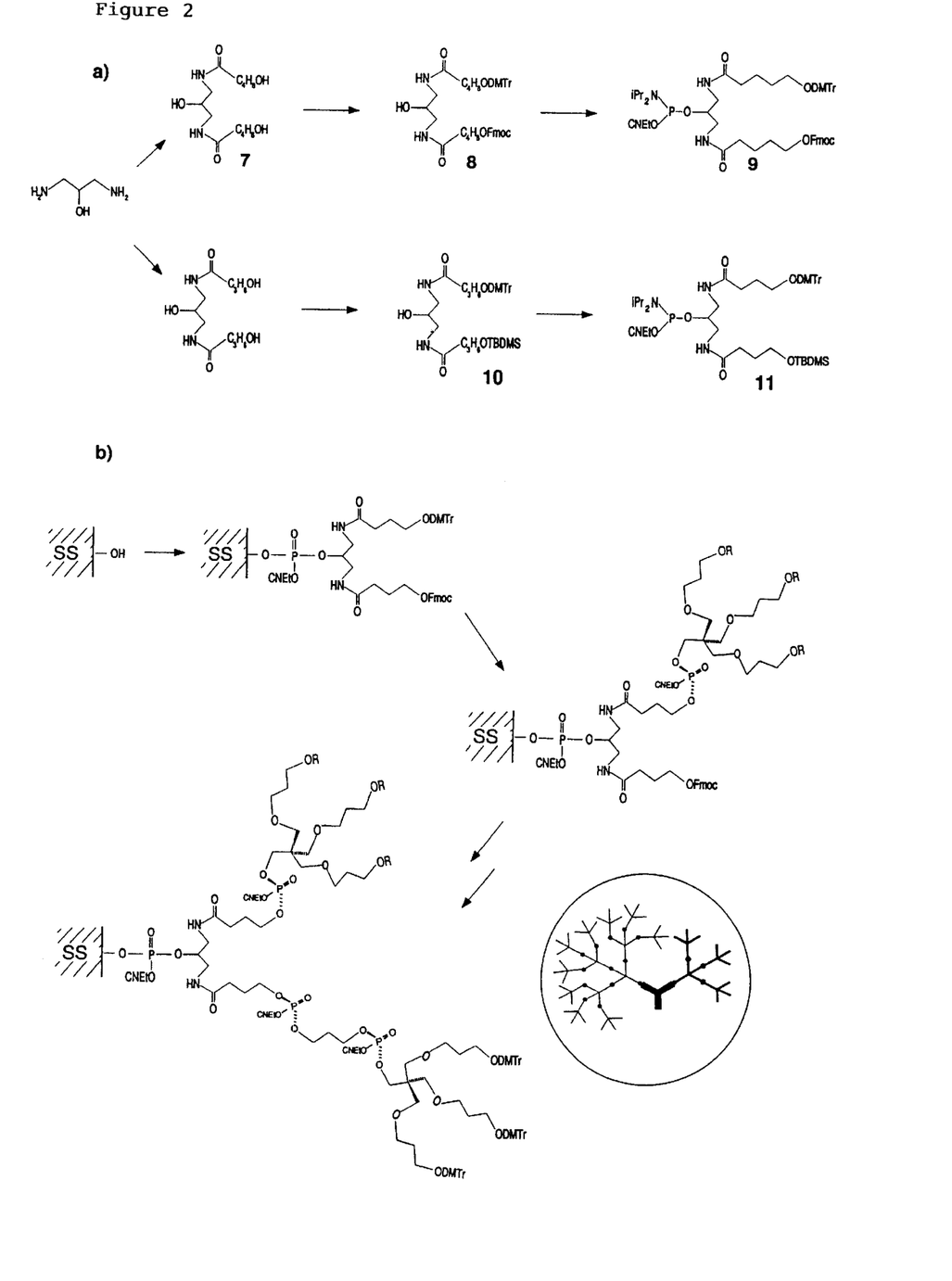
FIG. 2 illustrates the synthesis of different doubling reagents used in the invention and the synthesis of dendrimers using the doubling reagents.

A series of compounds have been made with three branched chains of different composition, thus giving three coupling sites, functionalised at the ends with different groups, and with different protective groups (FIG. 2). The compounds and their properties are:

N,N'-Di-(5-hydroxyvaleroyl)-1,3-diaminopropanol-2 (7). A solution of 3.28 g (36.4 mmol) of 1,3-diaminopropanol-2, 10 ml (100 mmol) of $\delta$-valerolactone (Acros/Fisher) and 75 mg (0.6 mmol) of DMAP in 60 ml of anhydrous MeOH was refluxed for 6 h and then kept overnight at rt. The reaction mixture was then evaporated, and an oily residue was dissolved in methylene chloride. The title compound was obtained as white crystalls after overnight at 4° C. Yield: 9.7 g (92%). Calculated for C13H26N2O5: 290.36. Mass-spectrum, MALDI-TOF: 313.039 (MI+Na+). Tm?!) IR (cm$^-$1): 1565 ($\theta$), 1635, 1645 (vc=o). $^1$H-NMR (DMSO-d6. $\delta$, md): 7.71 (br.t, 2 H, NH), 4.88 (d, 1 H, j=5 Hz, HOCH), 4.41 (t, 2 H, j=5 Hz, CH2OH), 3.49 (m, 1 H, OCH), 3,34 (m, 4 H, CH2O), 305 (m, 4 H. CH2N), 2.10 (t, 4 H, COCH2), 1.65–1.6 (m, 8 H, CH2CH2CH2OH).

N-[5-(9-Fmoc-oxy)valeroyl]-N'-[5-(4,4'-DMTr-oxy) valeroyl]-1,3-diaminopropanol-2 (8): Triol 7 (4.8 g, 16.5 mmol) was dried by coevaporation with anhydrous pyridine and dissolved in 60 ml of it. DMTrCl (3.7 g, 0.66 eqv) was added under stirring for 2 h at 0° C. In 5 h, 1 ml of water was added to the reaction mixture, it was stirred for another 10 min. and evaporated to an oil, dissolved in 200 ml of ethylacetate, washed with NaHCO3 sat. (4×200 ml), brine, dried over Na2SO4 and evaporated in vacuo. The resulting oil was purified by flash chromatography (dichloromethane to dichloromethane-methanol, 9:1) to give 4 g (62.5% for DMTrCl) of yellow solid, Rf 0.1 (MeOH-chloroform, 1:19). 2 g (3.38 mmol) of this diol was dried by coevaporation with anhydrous pyridine and dissolved in 30 ml of it. FmocCl (1 g, 3.87 mmol) was added under stirring at 0° C. In 2 h, 1 ml of water was added to the reaction mixture, it was stirred for another 10 min. and evaporated to an oil, dissolved in 200 mlof ethylacetate, washed with NaHCO3 sat. (4×200 ml), brine, dried over Na2SO4 and evaporated in vacuo. The resulting oil was purified by flash chromatography (dichloromethane to dichloromethane-methanol, 9:1) to give 2.2 g (80%) of white solid, Rf 0.69 (MeOH-chloroform, 1:19). Calc. (C49 H54N2O9): 814; MS: 837.398 (Ml+Na+). $^1$H-NMR(CDCl3, $\delta$, md): 7.85-6, 75(m,21 H, arom) 6.31, 6.28 (br.t.,2 H, NH), 4.43(d,2 H, CH2(Fl)), 4.3(d,1 H, OH), 4,2(t, 1 H, CHCH2(-Fl)), 3.8(s, 6 H, OCH3). 3.3 (m, 4 H, CH2N), 3.1 (m,1 H, HOCH),2.24 (m, 4 H,C(O)CH2), 1.7 (m, 12 H, OCH2CH2CH2).

N-[5-(9-Fluorenylmethoxycarbonyloxy)valeroyl]-N'-[5-(4,4'-Dimethoxytrityloxy)valeroyl]-2-0-(N,N-diisopropylamino-2-cyanethoxyphosphinyl)-1,3-diaminopropanol-2 (9) The alcohol 8 was phosphitylated using chloro[diisopropylamino]-β-cyanoethoxyphosphine as described elsewere and purified by flash chromatography (hexane:ethylacetate, 4:1, traces of Et3N) to give the title compound in 73% yield. Calc. (C58H71N4O10P):1014; MS:1037294. (MI+Na+).

N-[4-(TBDMS-oxy)butyryl]-N'-[4-(4,4'-DMTr-oxy) butyryl]-1,3-diaminopropanol-2 (10) N,N'-Di-(4-hydroxybutyryl)-1,3-diaminopropanol-2 was synthesised as described ( ). The key compound was synthesised as described for 8 using TBDMSCl instead of FmocCl. Yield for monotritylated product: 65% (for DMTrCl); Yield for the title compound (silylation): 83%. Calc.(C38H54N2O7Si): 679; MS: 701.787(MI+Na+). $^1$H-NMR (CDCl3, $\delta$, md): 7.48–6.76 (m, 13 H, arom.), 6.47, 6.36 (br.t,2 H, NH), 4.19 (m, 1 H, OH), 3.8 (s, 6 H, OCH3), 3.3 (m, 4 H, CH2N), 3.12 (p, 1 H, CHOH), 2.34 (m, 4 H, C(O)CH2), 1.88 (m, 8 H, CH2CH2O), 0.9 (s, 9 H, tBu), 0.06(s.6 H,Me).

N-[4-(tertbutyldimethoxysilyloxy)butyryl]-N'-[4-(4,4'-Dimethoxytrityloxy)butyrl]-2-0-(N,N-diisopropylamino-2-cyanethoxyphosphinyl)-1,3-diaminopropanol-2 (11) The alcohol was phosphitylated using chloro[diisopropylamino]-β-cyanoethyoxyphosphine as described elsewere and purified by flash chromatography (hexane:ethylacetate, 4:1, traces of Et3N) to give the title compound in 78% yield. Calc.(C47H71N4O8PSi): 879. MS:902.156 (MI+Na+).

Bifunctional Building Blocks

A series of compounds have been made with linear chains of different composition, thus giving two coupling sites, functionalised at the ends with different groups (FIG. 3). The compounds were synthesised according to previously published methods. The subclass of these compounds comprises the synthons bearing tagging or reporter groups, which generally have just one coupling site, thus serving as the terminators of branch growth.

Synthesis of Dendrimeric Structures

Examples of synthesis of plain oligonucleotide dendrimers. All synthetic cycles used were standard DNA synthesis protocols except for the waiting step which was increased to 2–3 min. Reagent 6 gives stable trebling of the amount of DMTr groups (>95% yield) for up to 3 condensations (Scheme 1, dendrimer of the third generation) when using 500 Å DMTrT-LCAA-CPG supports or up to 4–5 condensations when using a 1000 Å CPG supports and/or additional spacers (Scheme 3) between the surface and the branching point, thus giving 80–240 terminal functional groups (DMTr$^+$release control). The structure of the compound obtained after condensing the trebler to the 5'-OH-group of 5'-HO-T-LCAA-CPG and subsequent condensation of DMTrT-phosphoramidite to three hydroxyl groups of this dimer was confirmed by MALDI-TOFMS (3'-TpCH2C(CH2OCH2CH2CH2pT-5')3; Calc.(C54H81O35N8P4): 1526.151. MS: 1526.94 (MI+H$^+$)$^,$ 1548.94(MI+Na$^+$). Positive ion reflector mode, delay time of 80 nsec, 108 averaged scans). No trace of a product containing tow terminal thymidine residues instead of three, as would result from incomplete condensation, was detected.

Oligonucleotide synthesis (in either direction, using 3'- or 5'-phosphoramidite synthons) on top of dendrimeric structures produces 3,9, . . . 3$^n$ oligonucleotide moieties, were n is the number of generation.

Examples of synthesis of mixed oligonucleotide dendrimers. Dendrimers with different functionalities are synthesised using branching reagents bearing different protective groups. For example, to synthesise conjugatet dendrimers reagent 9 was condensed using usual synthetic cycle with elongated waiting step onto the CPG support already bearing pentaethyleneglycol linker. Then the DMTr-containing branch was deprotected and used as a coupling site for 6, which was in turn detritylated and DMTr$^+$release measured to check the yield (>95%). Three resulting OH- groups were capped (acetic anhydride/lutidine/THF/N-methylimidazole) using standard DNA synthesis operation. The Fmoc-protected branch was then deprotected using mild basic conditions as described. It was further condensed with propanediol phosphoramidite and then with 6 to give the structure shown on Scheme 2.

These examples illustrate how the simple building blocks can readily by used to extend branches alternately as required to produce the structures illustrate in FIGS. 4 to 6.

Examples of modulation of hydrophobicity by branched chain synthesis. Oligonucleotide 5'-TCT.TCT.TCT.TCT.TTT (SEQ ID NO:1) was synthesised on 0.2 μmol scale using 1000 Å CPG-support, to 5'-end of which the spacer molecule based on pentaethyleneglycol (FIG. 3) was attached. Starting from this step, we did not use the capping procedure. While still immobilised to CPG, this structure was detritylated and subjected to two condensations with "trebler" 6 (increased wait step), thus increasing the amount of 5'-OH-groups for each molecule up to nine. Then one half of the support was detritylated while the second half was left in DMTrON form. The two portions of CPG were then subjected to ammonolysis according to usual procedures.

The solution behaviour of the molecules was quite different. Nine DMTr-containing product readily formed a stable foam, whereas detritylated one did not. This is the expected behaviour. Clearly, 9 DMTrON compound would form a highly hydrophobic surface if left tethered on a solid support, whereas detritylated one would be hydrophilic. Surfaces with up to eight intermeidate degrees of hydrophilicity could readily be made using the strategy outlined on Scheme 6, selecting the appropriate programme to produce branched structures with the chosen level of DMTr substitution. As such surfaces useful? There is growing interest in carrying out chemical and biochemical procedures on a small scale in "laboratories on a chip"-devices on the nano to microscale. A major hurdle to the development of such devices is the problems of controlling liquid flow, and the associated problem of holding very small volumes of liquids in defined positions in the device. Liquids move to positions of lowest surface energy—it has been shown that liquids can move uphill against gravity along a surface tension gradient. The key to moving liquids on a surface is the ability to create features with appropriate surface energies in relation to the liquids involved. This can be fine tuned using the reagents which are the subject of this invention in the way described above. Surface coating agents with appropriate properties can be directed to the proper place on the surface either during synthesis e.g. using methods which are the subject of ref. 5 or by directing them to the proper place by e.g. the hybridisation interaction.

References

1. Whitesides, G. M., Mathias, J. P. and Seto, C. T. (1991) *Science*, 254, p.1312–1319. Ozin, G. (1992) *Adv. Mater.* 4, p.612–648. Mirkin, C. A., Letsinger, R. L., Mucic, R. C. and Stornhoff, J. J. (1996) *Nature,*382, p.607–609. Alivisatos, A. P., Johnsson, K. P. , Peng, X., Wilson, T. E., Loweth, C. J., Bruchez, M. P. and Schultz, P. G. (1996) *Nature,* 382, p.609–611. Terfort, A., Bowden, N. and Whitesides, G. M. (1997) *Science,* 276, p.233–235.

2. Newkome, G. R., Moorefield, C. N. and Vögtle, F. (1996) *Dendritic molecules: Concepts, Syntheses, perspectives.* VCH, N.Y.

3. McOmie, J. F. W. (1973) *Protective Groups in Organic Chemistry.* Plenum Press, London.

4. Brenner, S. and Lerner, R. A. (1992) *Proc. Natl. Acad. Sci. USA.* 89, p5381–5383.

5. Southern, E. M. (1993) Patent Appl. #93.15 847.5

6. Milner, N., Mir, K. U. and Southern, E. M. (1997) *Nature Biotechnol.* 15, p.537–541.

7. Southern, E. M., Maskos, U. and Elder, J. K., Johnson, M., Mir, K. U., Wang, L. and Williams, J. C. (1994) *Nucl. Acids Res.* 22, 1368–1373.

8. R. P. Haugland (1994) *Molecular Probes: Handbook of Fluorescent Probes and Research Chemicals.* 5th edition, 1992–1994. (Ed.: K. D. Larison) Molecular Probes, Inc.

What is claimed is:

1. A synthon selected from the group consisting of N-[5-(9-fluorenylmethoxycarbonyloxy)valeroyl]-N-[5-(4,4'-dimethoxytrityloxy)valeroyl]-2-O-(N,N-diisopropylamino-2-cyanethoxyphosphinyl)-1,3-diaminopropanol-2 and N-[4-(tertbutyldimethoxysilyloxy)-butyryl]-N'-[4-(4,4'-dimethoxytrityloxy)butyryl]-2-O-(N,N'-diisopropylamino-2-cyanethoxyphosphinyl-1,3-diaminopropanol-2.

2. A synthon which is tris-2,2,2-[3-(4,4'-dimethoxytrityloxy)propyloxymehtyl]-ethyl-N-N-diisopropylaminocyanethoxy phosphoramidite.

* * * * *

UNITED STATES PATENT AND TRADEMARK OFFICE
CERTIFICATE OF CORRECTION

PATENT NO. : 6,455,071 B1
DATED : September 24, 2002
INVENTOR(S) : Mikhail Sergeevich Shchepinov and Edwin Mellor Southern It is certified that error appears in the above-identified patent and that said Letters Patent is hereby corrected as shown below:

Column 16,
Lines 20-22, "tris-2,2,2-[3-(4,4'-dimethoxytrityloxy)propyloxymehtyl]-ethyl-N,N-diisopropylaminocyanethoxy phosphoramidite" should read -- tris-2,2,2-[3-(4,4'-dimethoxytrityloxy)propyloxymethyl]-ethyl-N,N-diisopropylaminocyanethoxy phosphoramidite --.

Signed and Sealed this

Tenth Day of December, 2002

JAMES E. ROGAN
*Director of the United States Patent and Trademark Office*

SEQUENCE LISTING

<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 1
tcttcttctt ctttt                                                    15